United States Patent
Hiraoka (10) Patent No.: US 11,344,184 B2
(45) Date of Patent: May 31, 2022

(54) ENDOSCOPE

(71) Applicant: OLYMPUS CORPORATION, Tokyo (JP)

(72) Inventor: Jin Hiraoka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 844 days.

(21) Appl. No.: 16/155,985

(22) Filed: Oct. 10, 2018

(65) Prior Publication Data

US 2019/0038114 A1    Feb. 7, 2019

Related U.S. Application Data

(63) Continuation of application No. PCT/JP2017/005758, filed on Feb. 16, 2017.

(30) Foreign Application Priority Data

Apr. 12, 2016    (JP) .............................. JP2016-079659

(51) Int. Cl.
*A61B 1/00*    (2006.01)
*G02B 23/24*    (2006.01)
(Continued)

(52) U.S. Cl.
CPC ...... *A61B 1/00137* (2013.01); *A61B 1/00098* (2013.01); *A61B 1/00142* (2013.01);
(Continued)

(58) Field of Classification Search
CPC ............ A61B 1/00089; A61B 1/00098; A61B 1/00101; A61B 1/00137
See application file for complete search history.

(56) References Cited

U.S. PATENT DOCUMENTS 5,562,600 A    10/1996  Matsuno
10,219,679 B2 *  3/2019  Tanaka ............... A61B 1/00098
(Continued)

FOREIGN PATENT DOCUMENTS

JP    H05-253177 A    10/1993
JP    H08-056900 A    3/1996
(Continued)

OTHER PUBLICATIONS

International Search Report dated May 9, 2017 issued in PCT/JP2017/005758.

*Primary Examiner* — Matthew J Kasztejna
(74) *Attorney, Agent, or Firm* — Scully, Scott, Murphy & Presser, P.C.

(57) ABSTRACT

An endoscope includes a distal-end hard portion at a distal end of an insert, including a body, housing, first and second grooves in the body to extend inwardly, and a through-hole communicating the first and second grooves in the housing; a forceps-raising table in the first groove, including a fitting-groove along a through-hole extending direction; an arm portion including a pillar extending from the second groove to the first groove, a fit-in portion fitted in the fitting-groove on one side, and a connecting portion on the other side, the connecting portion being connected with a forceps-operating wire; and a seal portion on a periphery of the pillar, sealing water-tightly a first gap and a second gap, the first gap being between a periphery of the pillar and a periphery defining the through-hole, and the second gap being between the periphery of the pillar and a periphery defining the fitting-groove.

13 Claims, 11 Drawing Sheets

(51) Int. Cl.
*A61B 17/00* (2006.01)
*A61B 17/29* (2006.01)

(52) U.S. Cl.
CPC ...... *G02B 23/2476* (2013.01); *A61B 1/00087* (2013.01); *A61B 17/29* (2013.01); *A61B 2017/0034* (2013.01)

(56) References Cited

U.S. PATENT DOCUMENTS

| | | |
|---|---|---|
| 2016/0206180 A1* | 7/2016 | Hosogoe .............. A61B 1/0057 |
| 2016/0270636 A1* | 9/2016 | Iwasaka ............. A61B 1/00137 |
| 2016/0270637 A1* | 9/2016 | Tanaka ............... A61B 1/00098 |
| 2017/0112363 A1* | 4/2017 | Morimoto ................ A61B 8/12 |
| 2018/0092512 A1* | 4/2018 | Hiraoka ............. A61B 1/00098 |
| 2020/0359880 A1* | 11/2020 | Hiraoka ............. A61B 1/00137 |

FOREIGN PATENT DOCUMENTS

| | | |
|---|---|---|
| JP | H11-151202 A | 6/1999 |
| JP | 2002-153420 A | 5/2002 |
| JP | 2015-165839 A | 9/2015 |

* cited by examiner

ENDOSCOPE

CROSS-REFERENCE TO RELATED APPLICATION

This application is a continuation of PCT International Application No. PCT/JP2017/005758 filed on Feb. 16, 2017 which claims the benefit of priority from Japanese Patent Application No. 2016-079659, filed on Apr. 12, 2016, the entire contents of which are incorporated herein by reference.

BACKGROUND

The present disclosure relates to an endoscope.

Endoscopes that are inserted into a body of a subject to perform observation and the like of a portion to be examined have been known in the past, and been used widely in a medical field, or the like. Some recent endoscopes have a raising mechanism to direct a treatment tool, such as a forceps, to give a medical treatment inside a subject body.

To prevent transmission of infectious diseases, it is necessary to clean endoscopes sufficiently before use. To improve cleanability of an endoscope, it is preferable that gaps between parts be sealed in a watertight manner. For example, Japanese Laid-open Patent Publication No. 11-151202 discloses an endoscope in which a periphery of a rotational axis is sealed with an O-ring.

SUMMARY

The present disclosure has been made in view of the above and is directed to an endoscope.

According to a first aspect of the present disclosure, an endoscope is provided which includes a distal-end hard portion arranged at a distal end of an insertion portion to be inserted to a subject, the distal-end hard portion including a main body formed of resin and a housing formed of metal, wherein a first groove and a second groove are formed in the main body so as to extend inwardly from an outer periphery, and wherein a through hole is formed in the housing so as to communicate the first groove and the second groove; a forceps raising table arranged in the first groove, the forceps raising table including a fitting groove formed along a direction in which the through hole extends; an arm portion including a pillar portion extending from the second groove to the first groove through the through hole, the pillar portion including a fit-in portion to be fitted in the fitting groove on one end side and a connecting portion on the other end side, the connecting portion being connected with a forceps operating wire that operates the forceps raising table; and a seal portion arranged on an outer periphery of the pillar portion of the arm portion, the sealing portion sealing a first gap and a second gap in a watertight manner, the first gap being formed between an outer peripheral surface of the pillar portion of the arm portion and an inner peripheral surface defining the through hole of the housing, and the second gap being formed between the outer peripheral surface of the pillar portion of the arm portion and an inner peripheral surface defining the fitting groove of the forceps raising table.

According to a second aspect of the present disclosure, an endoscope is provided which a forceps raising table; an arm portion including a connecting portion connected with a forceps operating wire that operates the forceps raising table; a distal-end hard portion arranged at a distal end of an insertion portion to be inserted to a subject, the distal-end hard portion including a main body formed of resin and a housing formed of metal, wherein a groove portion accommodating the forceps raising table and a space accommodating the arm portion are formed, and wherein a through hole is formed in the housing so as to communicate the groove portion and the space; a cap sealing the space of the distal-end hard portion; and a seal portion arranged on an outer periphery of a pillar portion of the arm portion, the seal portion sealing a first gap and a second gap in a watertight manner, the first gap being formed between an outer peripheral surface of the pillar portion of the arm portion and an inner peripheral surface defining the through hole of the housing, and the second gap being formed between the outer peripheral surface of the pillar portion of the arm portion and an inner peripheral surface defining the fitting groove of the forceps raising table.

According to a third aspect of the present disclosure, an endoscope is provide which includes a forceps raising table; an arm portion including a connecting portion connected with a forceps operating wire that operates the forceps raising table, and a through hole being open at one end into an interior space of the forceps raising table; a distal-end hard portion arranged at a distal end of an insertion portion to be inserted to a subject, the distal-end hard portion including a main body formed of resin and a housing formed of metal, wherein a groove portion accommodating the forceps raising table and a space accommodating the arm portion are formed, wherein the through hole is open at the other end into the space, and wherein another through hole that communicates the groove portion and the space is formed in the housing; a cap sealing the space of the distal-end hard portion; and a seal portion arranged on an outer periphery of a pillar portion of the arm portion, the seal portion sealing a first gap and a second gap in a watertight manner, the first gap being formed between an outer peripheral surface of the pillar portion of the arm portion and an inner peripheral surface defining the through hole of the housing, and the second gap being formed between the outer peripheral surface of the pillar portion of the arm portion and an inner peripheral surface defining the fitting groove of the forceps raising table.

The above and other features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Embodiments of an endoscope according to the present disclosure are explained, referring to the drawings. The embodiments are not intended to limit the present disclosure. The present disclosure can be applied to general endoscopes that use a treatment tool, such as a forceps, to give a treatment inside a body of a subject.

Moreover, like reference symbols are assigned to like components throughout the drawings. The drawings are schematic illustration, and it is noted that a relationship in size of respective components, a ratio of the respective components, and the like can be different from an actual situation. In addition, sizes and ratios can be different from each other among the drawings also.

Embodiment

Figure 1:
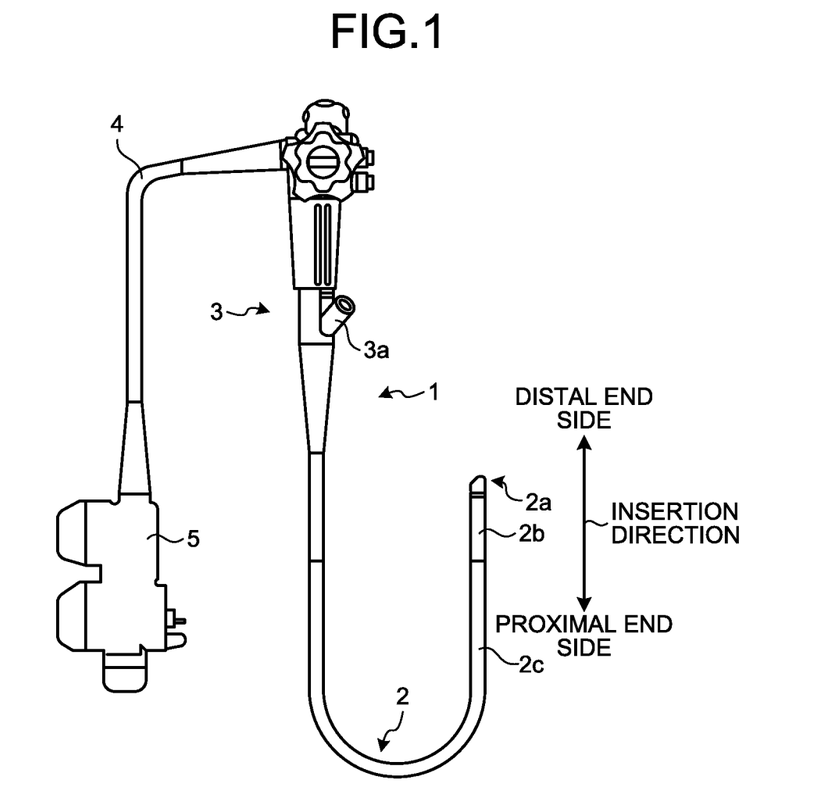
FIG. 1 is a schematic view illustrating a configuration of an endoscope according to an embodiment of the present disclosure.

FIG. 1 is a schematic view illustrating a configuration of an endoscope according to an embodiment of the present disclosure. An endoscope 1 includes an insertion portion 2 that is provided at a distal end with an imaging device and inserted into a subject, an operating unit 3 that is provided continuously on a side of a proximal end of this insertion portion 2, a universal cord 4 that extends from a side portion of this operating unit 3, and a connector portion 5 that is provided continuously to the universal cord 4 and connected to an observation apparatus to control the endoscope 1 and a light source apparatus to provide illumination light to the endoscope 1, and the like. Here, a direction that is a longitudinal direction of the endoscope and in which the insertion portion 2 is inserted into the body of the subject is referred to as "insertion direction", and a side of the distal end in the insertion direction (upper side in FIG. 1) is referred to as "distal end side", and a side of the proximal end (lower side in FIG. 1) is referred to as "proximal end side" as shown in FIG. 1.

The insertion portion 2 includes a distal end portion 2a, a bent portion 2b that is structured to be bendable according to an operation of the operating unit 3, and a flexible tube portion 2c that is flexible in this order from the distal end side. A proximal end of the flexible tube portion 2c is provided continuously to a distal end side of the operating unit 3.

The operating unit 3 has a forceps insertion inlet 3a to insert forceps needles or the like, which is a treatment tool, into the subject. Inside the insertion portion 2, a forceps inserting path is provided, and the forceps insertion inlet 3a functions as an insertion entrance of the forceps inserting path. Furthermore, the operating unit 3 accepts an operation to rotate a rotation axis described later.

Figure 2:
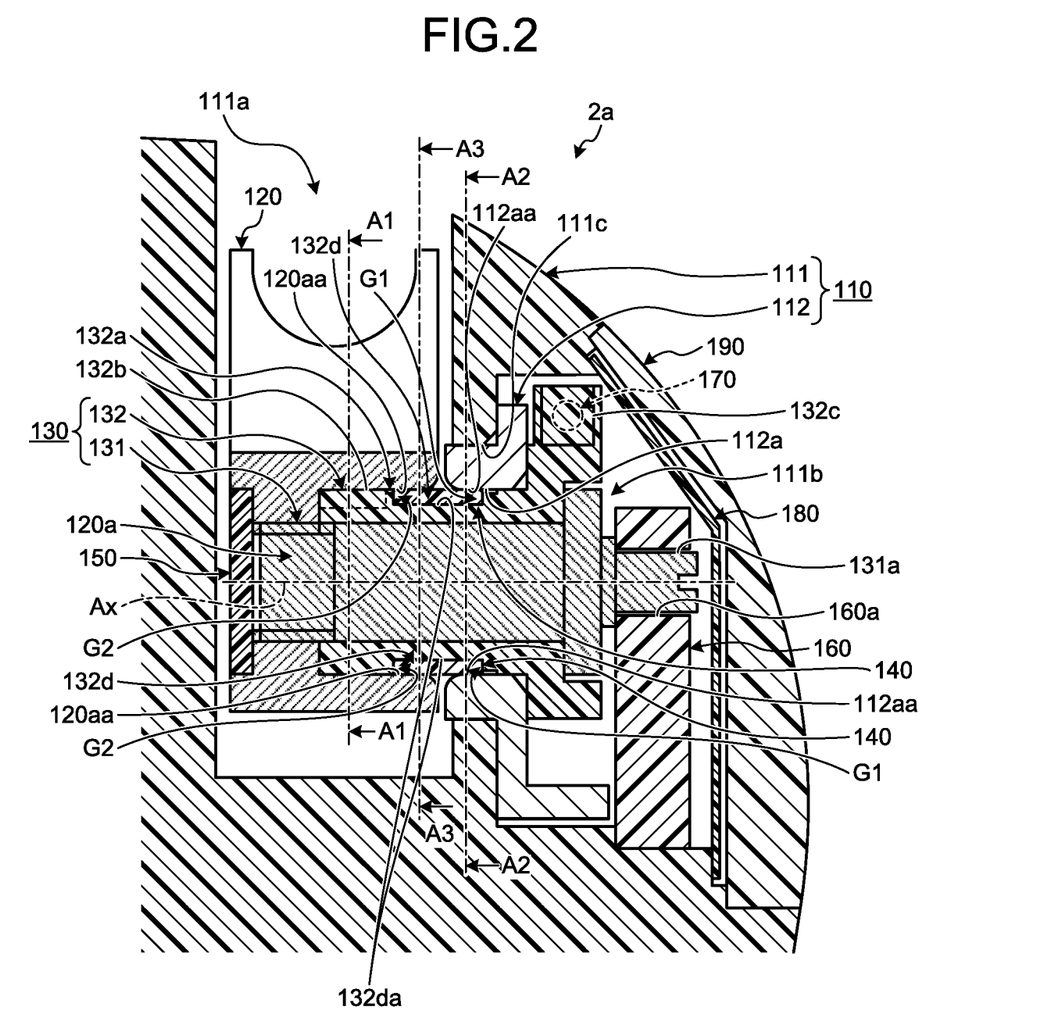
FIG. 2 is a schematic partial cross-sectional view of a distal end portion of the endoscope shown in FIG. 1.

FIG. 2 is a schematic partial cross-sectional view illustrating the distal end portion of the endoscope shown in FIG. 1. FIG. 2 shows a cross section perpendicular to the insertion direction. As shown in FIG. 2, the distal end portion 2a includes a distal-end hard portion 110 that is arranged at an end of the distal end portion 2a, a forceps raising table 120 to raise a forceps that protrudes out from the distal-end hard portion 110, an arm portion 130 that is engaged with the forceps raising table 120 rotatably therewith, a seal portion 140 that seals gaps between the distal-end hard portion 110 and the arm portion 130, and between the forceps raising table 120 and the arm portion 130 in a watertight manner, a forceps raising-table cap 150 that is connected to the forceps raising table 120, a bearing 160 that rotatably supports the arm portion 130, a forceps manipulating wire 170 that is connected to the arm portion 130, a cap 190 that closes a portion on a side of the forceps manipulating wire 170 from the seal portion 140 of the arm portion 130 in a watertight manner with an adhesive, and a cover 180 that prevents the adhesive and the like from flowing to the inside of the distal-end hard portion 110 from the cap 190 side.

The distal-end hard portion 110 has a main body 111 that is made from, for example, resin, and a housing 112 that is made from, for example, metal. The materials of the main body 111 and the housing 112 are not limited to resin and metal. The main body 111 may be made from a metal and the housing 112 may be made from ceramic. Furthermore, the main body 111 and the housing 112 may be formed integrally with metal. In the main body 111, a first groove 111a and a second groove 111b are formed which extend from a periphery toward the inside. The extending directions of the first and second grooves 111a, 111b are perpendicular to each other. Moreover, at a bottom portion of the second groove 111b of the main body 111, an opening 111c is formed. The housing 112 is fixed to an inner side of the opening 111c of the main body 111 by an adhesive or the like. In the housing 112, a through hole 112a that communicates a side surface of the first groove 111a and a bottom surface of the second groove 111b is formed.

The forceps raising table 120 is arranged to be housed in the first groove 111a. In the forceps raising table 120, a fitting groove 120a is formed along a direction in which the through hole 112a extends.

Figure 3:
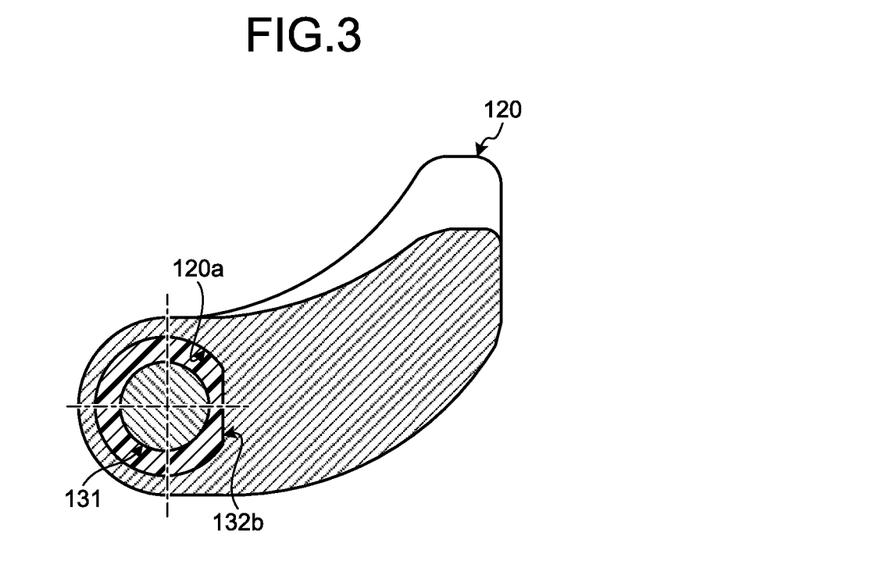
FIG. 3 is a partial cross-sectional view taken along a line A1-A1 in FIG. 2.

The arm portion 130 includes a first member 131 and a second member 132. The first member 131 is a pillar member that extends along a rotation axis Ax. A shaft 131a positioned at one side of the first member 131 is rotatably supported by a shaft hole 160a that is formed in the bearing 160. The second member 132 is arranged to cover a periphery of a central portion of the first member 131, and is fixed to the first member 131 by an adhesive or the like. The second member 132 has a pillar portion 132a that extends from the second groove 111b to the first groove 111a through the through hole 112a. On one side (closer to the first groove 111a) of the pillar portion 132a of the second member 132, a fit-in portion 132b to be fitted in the fitting groove 120a of the forceps raising table 120 is formed. FIG. 3 is a partial cross-sectional view taken along a line A1-A1 in FIG. 2. As shown in FIG. 3, an outer peripheral shape of the fit-in portion 132b and an inner peripheral shape of the fitting groove 120a have a D-cut shape formed of a curved part and a straight part. The fit-in portion 132b is fitted in the fitting groove 120a so that relative rotation of the fit-in portion 132b and the fitting groove 120a is prevented. As long as the relative rotation of the fit-in portion 132b and the fitting groove 120a is prevented, the outer peripheral shape of the fit-in portion 132b and the inner peripheral shape of the fitting groove 120a are not necessarily completely the same with each other. On the opposite side of the fit-in portion 132b of the pillar portion 132a of the second member 132 (on a side closer to the second groove 111b), a connecting portion 132c is formed. The forceps manipulating wire 170 is connected to the connecting portion 132c. As a result, when an operation is input to the operating unit 3 and the forceps manipulating wire 170 is pulled to the proximal end side, the arm portion 130 and the forceps raising table 120 rotate together to raise the forceps protruding from the distal-end hard portion 110. In the pillar portion 132a of the second member 132, a concave portion 132d is formed. The seal portion 140 is fitted in the concave portion 132d.

Figure 4:
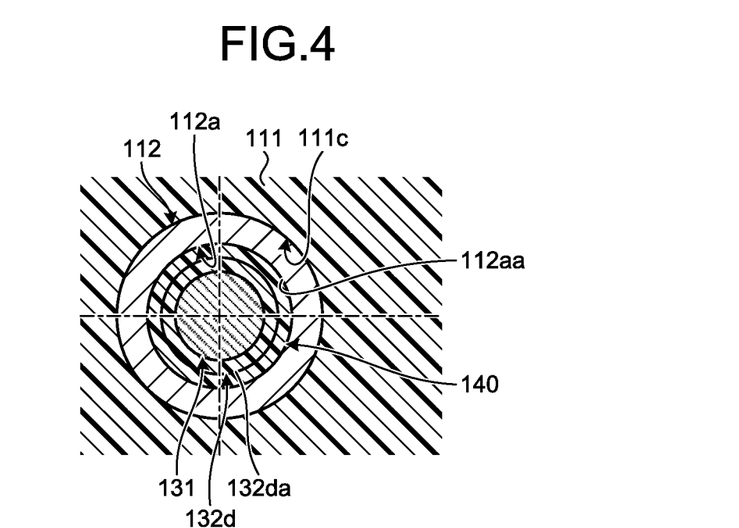
FIG. 4 is a partial cross-sectional view taken along a line A2-A2 in FIG. 2.
Figure 5:
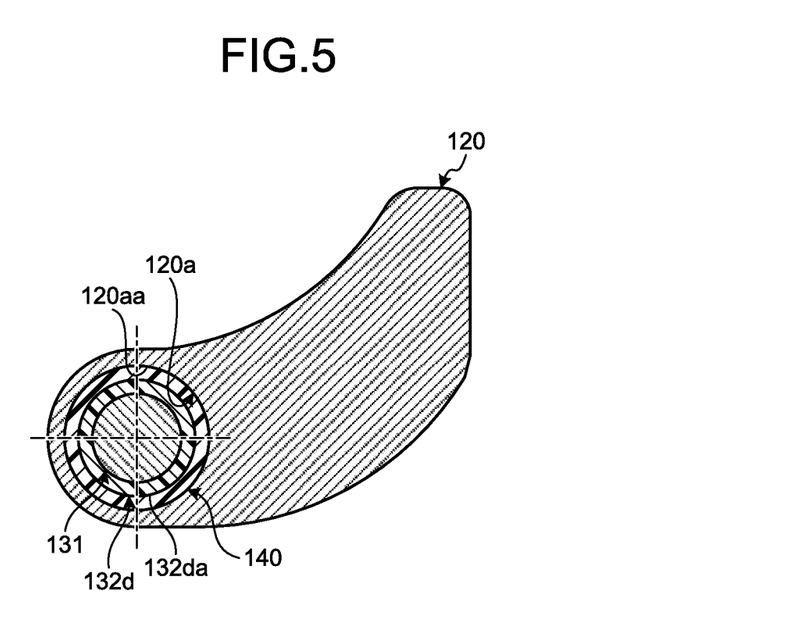
FIG. 5 is a partial cross-sectional view taken along a line A3-A3 in FIG. 2.

The seal portion 140 is made of a material having elasticity, such as silicone, and is arranged on a periphery of the pillar portion 132a of the arm portion 130 (the second member 132). FIG. 4 is a partial cross-sectional view taken along a line A2-A2 in FIG. 2. As shown in FIG. 4, the seal portion 140 seals a first gap G1 (refer to FIG. 2) formed between a bottom surface 132da of the concave portion 132d, which is an outer peripheral surface of the pillar portion 132a of the arm portion 130, and an inner peripheral surface 112aa forming the through hole 112a of the distal-end hard portion 110 (the housing 112) in a watertight manner. FIG. 5 is a partial cross-sectional view taken along a line A3-A3 in FIG. 2. As shown in FIG. 5, the seal portion 140 seals a second gap G2 (refer to FIG. 2) formed between the bottom surface 132da of the concave portion 132d, which is the outer peripheral surface of the pillar portion 132a of the arm portion 130, and an inner peripheral surface 120aa forming the fitting groove 120a of the forceps raising table 120 in a watertight manner.

As explained above, according to the embodiment, the seal portion 140 seals the first gap G1 and the second gap G2 in a watertight manner integrally (or in unison). Therefore, the number of assembling processes can be reduced compared to a case where the first gap G1 and the second gap G2 are sealed with two members, respectively, in a watertight manner. Accordingly, the endoscope 1 according to the embodiment provides favorable cleanability with a simple structure.

First Modification

Figure 6:
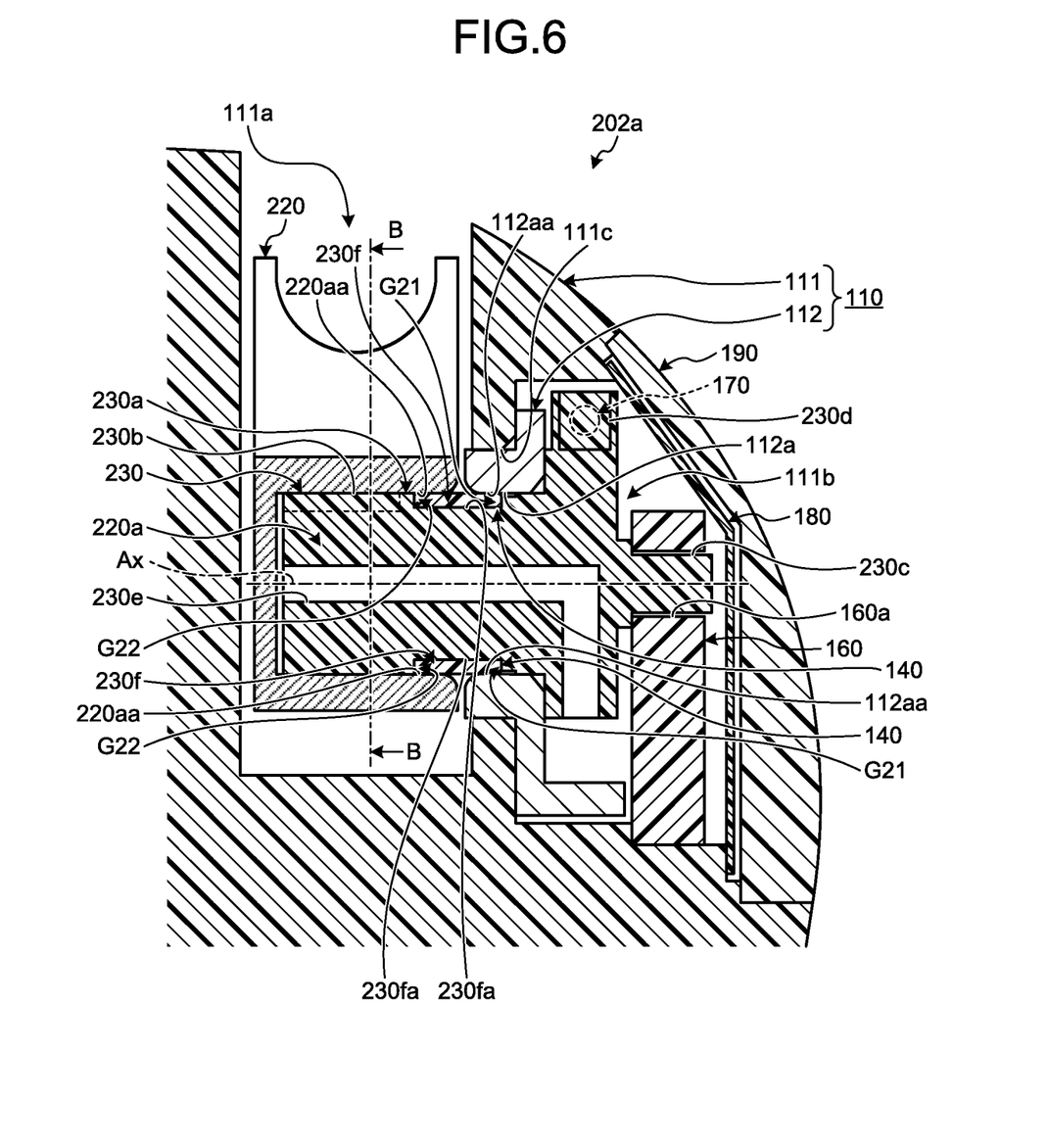
FIG. 6 is a schematic partial cross-sectional view illustrating a distal end portion of an endoscope according to a first modification of the embodiment.

FIG. 6 is a schematic partial cross-sectional view illustrating a distal end portion of an endoscope according to a first modification of the foregoing embodiment. The endoscope according to the first modification has the same configuration as the embodiment, except a part of a distal-end portion 202a and, therefore, explanation is omitted as appropriate.

Figure 7:
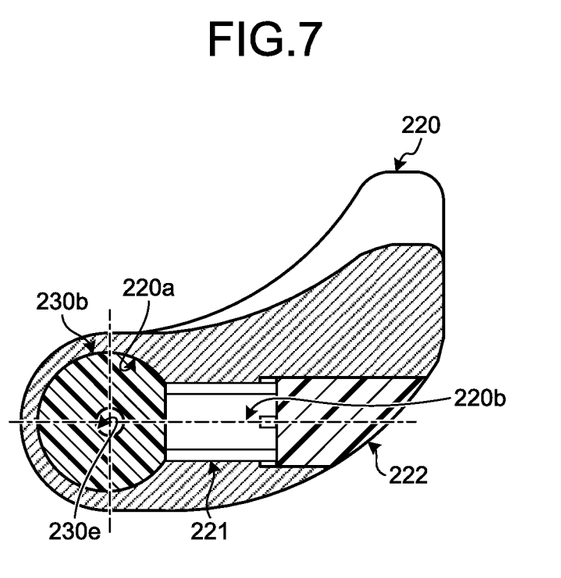
FIG. 7 is a partial cross-sectional view taken along a line B-B in FIG. 6.

In a forceps raising table 220, a fitting groove 220a is formed along a direction in which the through hole 112a extends. FIG. 7 is a partial cross-sectional view taken along a line B-B in FIG. 6. As shown in FIG. 7, in the forceps raising table 220, a screw hole 220b that communicates with the fitting groove 220a inside is formed. A screw 221 is screwed in the screw hole 220b, and the screw 221 thereby presses a fit-in portion 230b of an arm portion 230 described later. As a result, relative rotation of the fit-in portion 230b and the fitting groove 220a is prevented. Furthermore, the screw hole 220b is sealed with a locking member 222 to prevent loosening of the screw 221.

Referring back to FIG. 6, the arm portion 230 of the distal end portion 202a is structured with a single member, unlike the foregoing embodiment. The arm portion 230 has a pillar portion 230a that extends from the second groove 111b to the first groove 111a through the through hole 112a. On one side (closer to the first groove 111a) of the pillar portion 230a, the fit-in portion 230b that is fitted in the fitting groove 220a of the forceps raising table 220 is formed. The fit-in portion 230b has a cross-sectional shape of a D-cut shape formed of a curved part and a straight part as shown in FIG. 7. On the other side (closer to the second groove 111b) of the fit-in portion 230b of the pillar portion 230a, a shaft 230c that is rotatably supported by the shaft hole 160a formed in the bearing 160, and a connecting portion 230d that is connected to the forceps manipulating wire 170 are formed. Inside the pillar portion 230a, a hole 230e for leakage test is formed. In the pillar portion 230a, a concave portion 230f in which the seal portion 140 is fitted is formed.

The seal portion 140 seals a first gap G21 formed between a bottom surface 230fa of the concave portion 230f, which is an outer peripheral surface of the pillar portion 230a of the arm portion 230, and the inner peripheral surface 112aa forming the through hole 112a of the distal-end hard portion 110 (the housing 112) in a watertight manner. The seal portion 140 seals a second gap G22 formed between the bottom surface 230fa of the concave portion 230f, which is the outer peripheral surface of the pillar portion 230a of the arm portion 230, and an inner peripheral surface 220aa forming the fitting groove 220a of the forceps raising table 220 in a watertight manner.

As described above, according to the first modification, the seal portion 140 integrally seals the first gap G21 and the second gap G22 in a watertight manner. Therefore, the number of assembling processes can be reduced compared to a case where the first gap G21 and the second gap G22 are sealed with two members, respectively, in a watertight manner. Accordingly, the endoscope 1 according to this modification also provides favorable cleanability with a simple structure.

Second Modification

Figure 8:
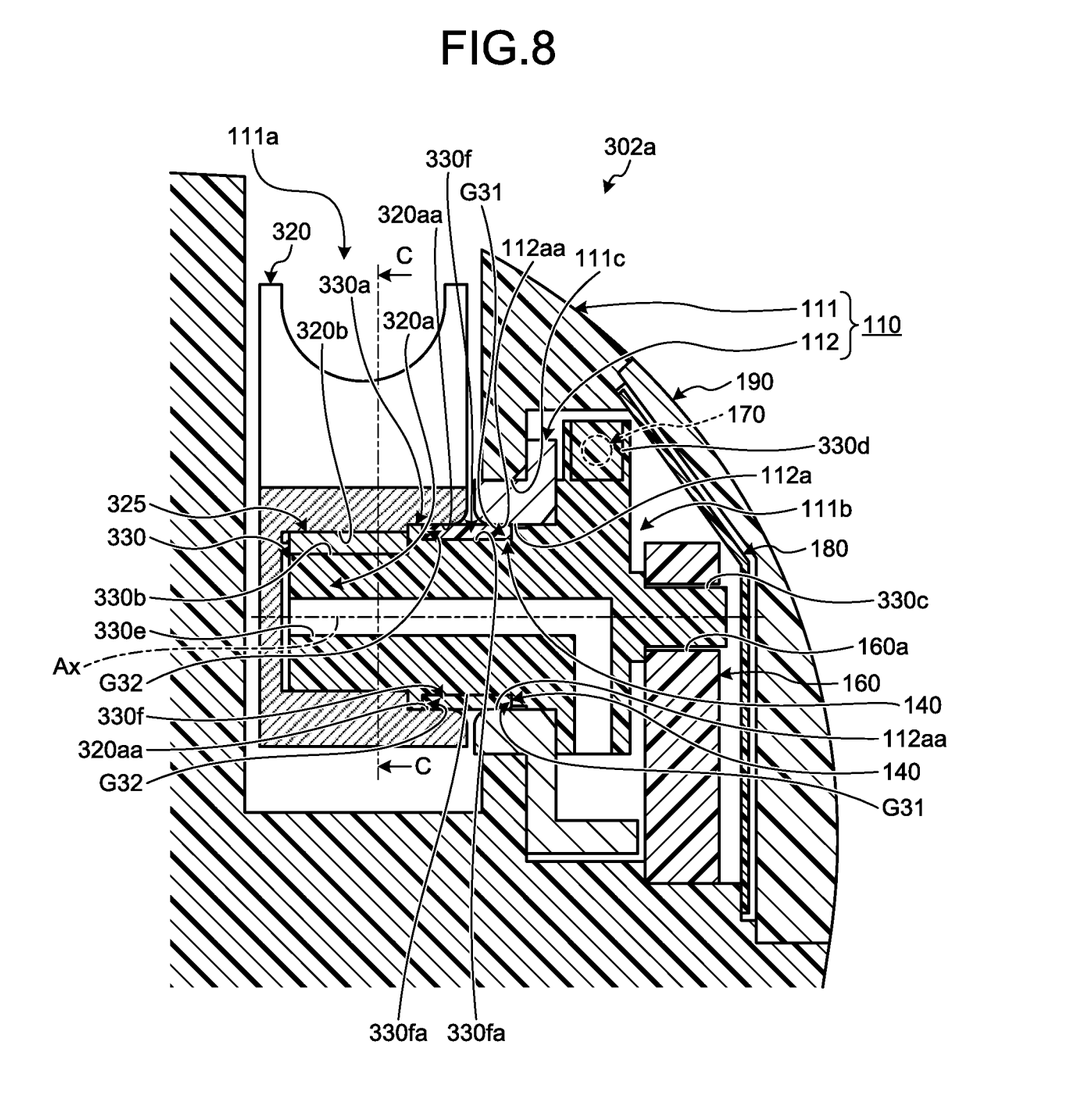
FIG. 8 is a schematic partial cross-sectional view illustrating a distal end portion of an endoscope according to a second modification of the embodiment.

FIG. 8 is a schematic partial cross-sectional view illustrating a distal end portion of an endoscope according to a second modification of the foregoing embodiment. The endoscope according to the second modification has the same configuration as the foregoing embodiment, except a part of a distal-end portion 302a and, therefore, explanation is omitted as appropriate.

Figure 9:
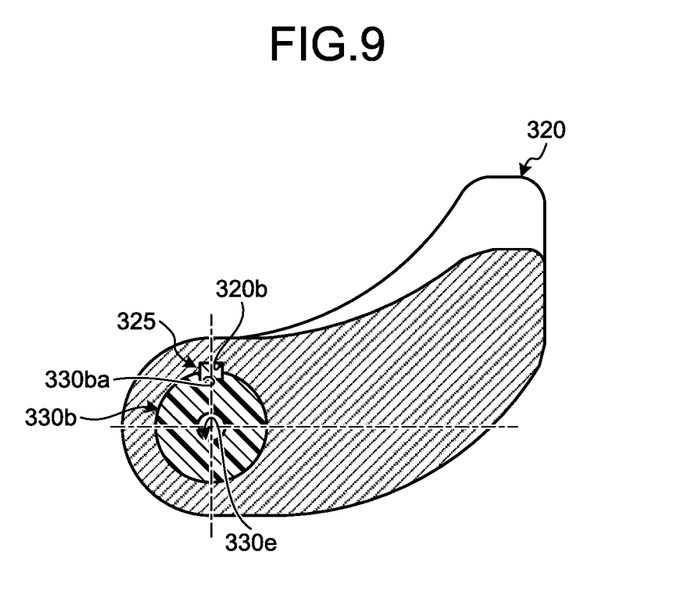
FIG. 9 is a partial cross-sectional view taken along a line C-C in FIG. 8.

In a forceps raising table 320, a fitting groove 320a is formed along the direction in which the through hole 112a extends. FIG. 9 is a partial cross-sectional view taken along a line C-C in FIG. 8. As shown in FIG. 9, in the forceps raising table 320, a notch 320b is formed in the direction in which the through hole 112a extends.

Referring back to FIG. 8, an arm portion 330 of the distal end portion 302a is structured with a single member, unlike the foregoing embodiment. The arm portion 330 has a pillar portion 330a that extends from the second groove 111b to the first groove 111a through the through hole 112a. On one side (closer to the first groove 111a) of the pillar portion 330a, a fit-in portion 330b that is fitted in the fitting groove 320a of the forceps raising table 320 is formed. The fit-in portion 330b has a notch 330ba (FIG. 9) formed therein along the direction in which the through hole 112a extends. On the other side (closer to the second groove 111b) of the fit-in portion 330b of the pillar portion 330a, a shaft 330c that is rotatably supported by the shaft hole 160a formed in the bearing 160, and a connecting portion 330d that is connected to the forceps manipulating wire 170 are formed. Inside the pillar portion 330a, a hole 330e for leakage test is formed. In the pillar portion 330a, a concave portion 330f in which the seal portion 140 is fitted is formed.

As shown in FIG. 9, between a pair of the notches 320b, 330ba formed to oppose to each other, a rotation preventing member 325 is inserted. As a result, relative rotation of the fit-in portion 330b and the fitting groove 320a is prevented.

The seal portion 140 seals a first gap G31 formed between a bottom surface 330fa of the concave portion 330f, which is an outer peripheral surface of the pillar portion 330a of the arm portion 330, and the inner peripheral surface 112aa forming the through hole 112a of the distal-end hard portion 110 (the housing 112) in a watertight manner. The seal portion 140 seals a second gap G32 formed between the bottom surface 330fa of the concave portion 330f, which is the outer peripheral surface of the pillar portion 330a of the arm portion 330, and an inner peripheral surface 320aa forming the fitting groove 320a of the forceps raising table 320 in a watertight manner.

As explained above, according to the second modification, the seal portion 140 integrally seals the first gap G31 and the second gap G32 in a watertight manner. Therefore, the number of assembling processes can be reduced compared with a case where the first gap G31 and the second gap G32 are sealed with two members, respectively, in a watertight manner. Accordingly, the endoscope 1 according to this modification also provides favorable cleanability with a simple structure.

Third Modification

Figure 10:
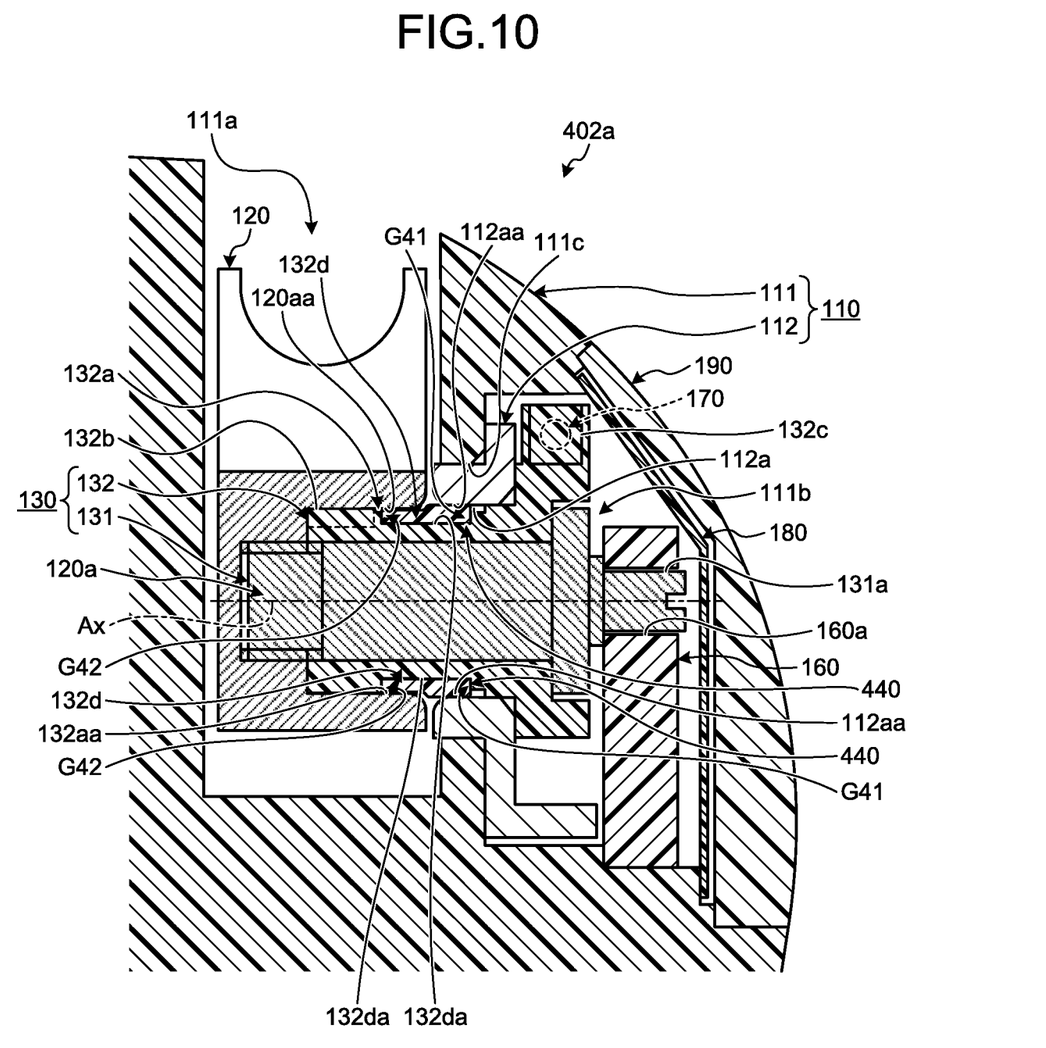
FIG. 10 is a schematic partial cross-sectional view illustrating a distal end portion of an endoscope according to a third modification of the embodiment.

FIG. 10 is a schematic partial cross-sectional view illustrating a distal end portion of an endoscope according to a third modification of the foregoing embodiment. The endoscope according to the third modification has the same configuration as the embodiment, except a part of a distal-end portion 402a and, therefore, explanation is omitted as appropriate.

In the distal end portion 402a, a first gap G41 formed between the pillar portion 132a of the arm portion 130 and the through hole 112a of the distal-end hard portion 110 (the housing 112) is larger in width in all directions on a plane perpendicular to the rotation axis Ax (or in a radial direction from the rotation axis Ax) than a second gap G42 formed between the pillar portion 132a of the arm portion 130 and the fitting groove 120a of the forceps raising table 120.

The seal portion 330 is formed to be thicker at one end than the other end, and seals the first gap G41 and the second gap G42 having different widths in a watertight manner at the same time.

As explained above, according to the third modification, a seal portion 440 integrally seals the first gap G41 and the second gap G42 in a watertight manner. Therefore, the number of assembling processes can be reduced from a case of sealing the first gap G41 and the second gap G42 with two members, respectively, in a watertight manner. Accordingly, the endoscope 1 according to this modification also provides favorable cleanability with a simple structure.

With the configuration of the third modification, by forming the seal portion 440 thin on the side of the forceps raising table 120, it is possible to prevent, more certainly, the watertightness on the side of the distal-end hard portion 110 from being deteriorated due to deformation of the seal portion 440 caused as the forceps raising table 120 moves.

Fourth Modification

Figure 11:
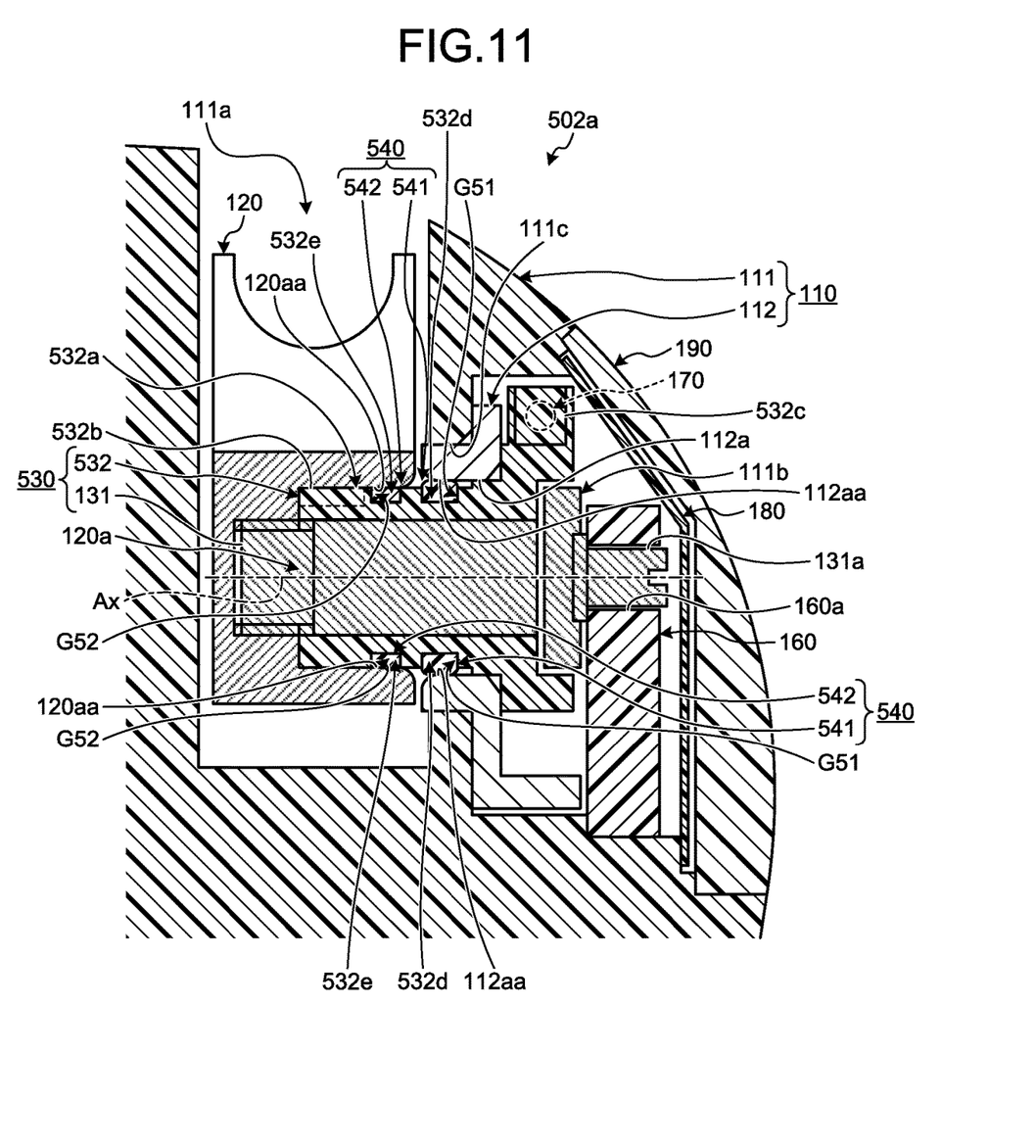
FIG. 11 is a schematic partial cross-sectional view illustrating a distal end portion of an endoscope according to a fourth modification of the embodiment.

FIG. 11 is a schematic partial cross-sectional view illustrating a distal end portion of an endoscope according to a fourth modification of the foregoing embodiment. The endoscope according to the fourth modification has the same configuration as the embodiment, except a part of a distal-end portion 502a and, therefore, explanation is omitted as appropriate.

In the distal end portion 502a, a first gap G51 formed between a pillar portion 532a of an arm portion 530 and the through hole 112a of the distal-end hard portion 110 (the housing 112) is larger in width in all directions on a plane perpendicular to the rotation axis Ax (or in a radial direction from the rotation axis Ax) than a second gap G52 formed between the pillar portion 532a of the arm portion 530 and the fitting groove 120a of the forceps raising table 120.

The arm portion 530 includes the first member 131 and a second member 532. The second member 532 is arranged to cover a periphery of the central portion of the first member 131, and is fixed to the first member 131 with an adhesive or the like. The second member 532 includes a pillar portion 532a that extends from the second groove 111b to the first groove 111a through the through hole 112a. On one side (closer to the first groove 111a) of the pillar portion 532a of the second member 532, a fit-in portion 532b that is fitted in the fitting groove 120a of the forceps raising table 120 is formed. On the other side (closer to the second groove 111b) of the fit-in portion 532b of the pillar portion 532a of the second member 532, a connecting portion 532c that is connected to the forceps manipulating wire 170 are formed. In the pillar portion 532a of the second member 532, a first concave portion 532d and a second concave portion 532e in which a seal portion 540 is fitted are formed.

The seal portion 540 is constituted of a first seal portion 541 that is fitted in the first concave portion 532d and a second seal portion 542 that is fitted in the second concave portion 532e. Thus, the seal portion 540 may be structured as separate members.

Figure 12:
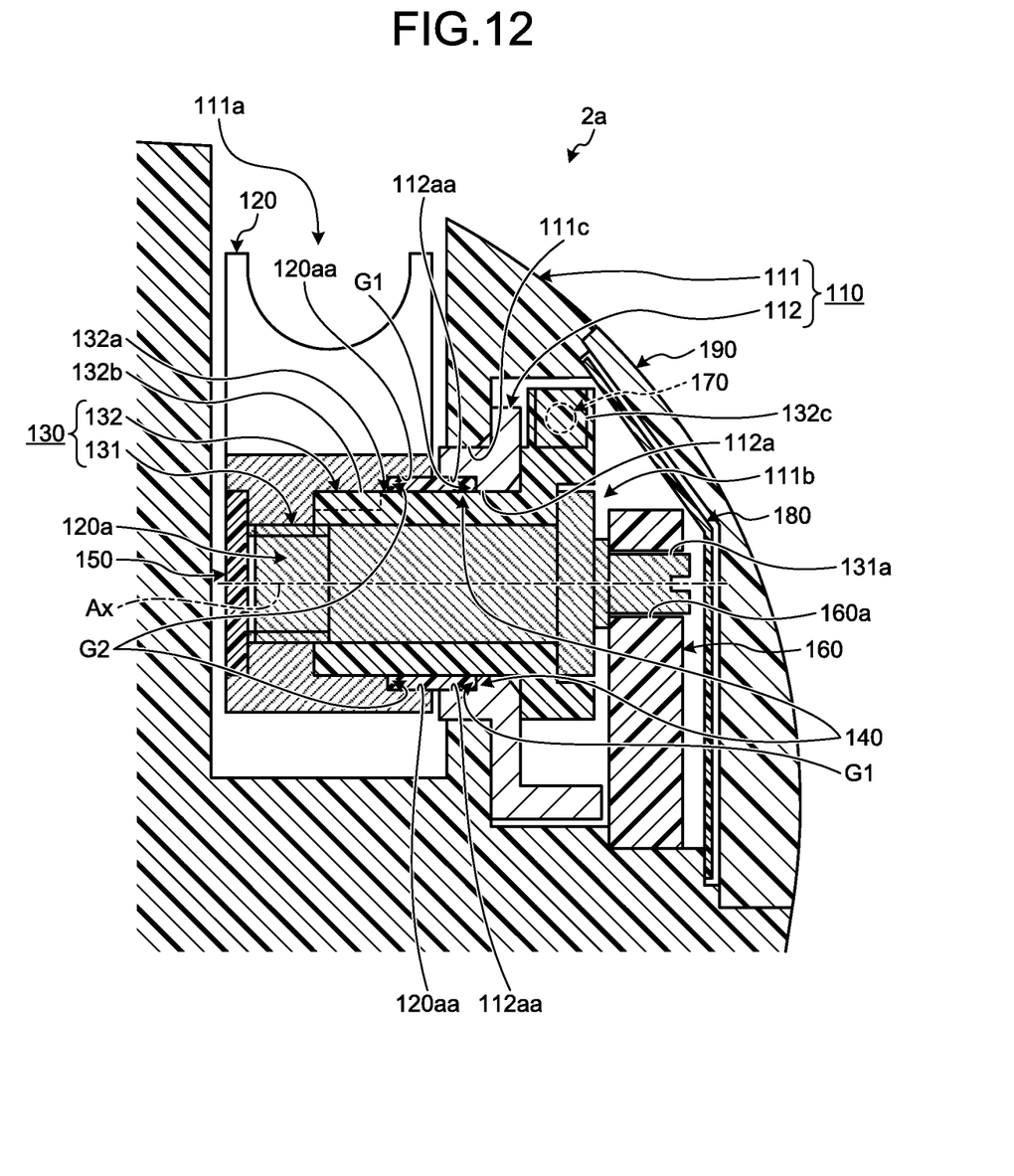
FIG. 12 shows another example of the embodiment.

Although a structure in which a concave portion is formed in a pillar portion, and a seal portion is fitted in the concave portion of the pillar portion has been explained in the above embodiment, it is not limited thereto. FIG. 12 shows another example of the embodiment. As shown in FIG. 12, it can be structured such that a concave portion is formed on a side of the forceps raising table 120 and the distal-end hard portion 110 (the housing 112), and the seal portion 140 is fitted in the concave portion of the forceps raising table 120 and the distal-end hard portion 110.

According to the present disclosure, an endoscope in a simple structure and excellent cleanability can be provided.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   a distal-end hard portion arranged at a distal end of an insertion portion configured to be inserted into a subject, the distal-end hard portion including a main body formed of resin and a housing formed of metal, wherein a first groove and a second groove are formed in the main body so as to extend inwardly from an outer periphery, and wherein a through hole is formed in the housing so as to communicate the first groove and the second groove;
   a forceps raising table rotatably arranged in the first groove, the forceps raising table including a fitting groove formed along a direction in which the through hole extends;
   an arm including a pillar portion extending from the second groove to the first groove through the through hole, the pillar portion including a fit-in portion to be fitted in the fitting groove on one end side and a connecting portion on the other end side, the connecting portion being connected with a forceps operating wire that operates the forceps raising table; and a single unitary seal arranged on an outer periphery of the pillar portion of the arm, the seal including a first portion provided to a first gap and a second portion provided to a second gap, the seal sealing the first gap and the second gap in a watertight manner, the first gap being formed between an outer peripheral surface of the pillar portion of the arm and an inner peripheral surface defining the through hole of the housing, and the second gap being formed between the outer peripheral surface of the pillar portion of the arm and an inner peripheral surface defining the fitting groove of the forceps raising table.

2. The endoscope according to claim 1, wherein a concave portion in which the seal is fitted is formed in the pillar portion.

3. The endoscope according to claim 1, wherein an outer periphery shape of the fit-in portion matches with an inner periphery shape of the fitting groove to prevent relative rotation of the fit-in portion and the fitting groove.

4. The endoscope according to claim 1, further comprising a screw hole formed in the forceps raising table, the screw hole communicating with the fitting groove, wherein the screw is screwed into the screw hole to press the fit-in portion to prevent relative rotation of the fit-in portion and the fitting groove.

5. The endoscope according to claim 1, further comprising:
a pair of notches formed in the fit-in portion and the fitting groove, respectively, the pair of notches opposing to each other and extending along a direction in which the through hole of the housing extends; and
a rotation preventing member is inserted between the pair of notches.

6. The endoscope according to claim 1, wherein the seal varies in thickness along a direction in which the through hole extends.

7. The endoscope according to claim 1, wherein the seal integrally seals the first gap and the second gap in a watertight manner.

8. The endoscope according to claim 1, further comprising a forceps raising table cap attached to the forceps raising table.

9. The endoscope according to claim 1, wherein the pillar portion is provided with a hole for a leakage test.

10. The endoscope according to claim 1, further comprising a bearing including a shaft hole that rotatably supports the arm.

11. The endoscope according to claim 1, wherein the fit-in portion of the arm is fitted in the fitting groove of the forceps raising table arranged in the first groove from the second groove.

12. An endoscope comprising:
a forceps raising table;
an arm including a connecting portion connected with a forceps operating wire that operates the forceps raising table;
a distal-end hard portion arranged at a distal end of an insertion portion configured to be inserted into a subject, the distal-end hard portion including a main body formed of resin and a housing formed of metal, wherein a groove portion accommodating the forceps raising table and a space accommodating the arm are formed, and wherein a through hole is formed in the housing so as to communicate the groove portion and the space;
a cap sealing the space of the distal-end hard portion; and
a single unitary seal arranged on an outer periphery of a pillar portion of the arm, the seal including: a first portion provided to a first gap; and a second portion provided to a second gap, the seal sealing the first gap and the second gap in a watertight manner, the first gap being formed between an outer peripheral surface of the pillar portion of the arm and an inner peripheral surface defining the through hole of the housing, and the second gap being formed between the outer peripheral surface of the pillar portion of the arm and an inner peripheral surface defining the fitting groove of the forceps raising table.

13. An endoscope comprising:
a forceps raising table;
an arm including a connecting portion connected with a forceps operating wire that operates the forceps raising table, and a through hole being open at one end into an interior space of the forceps raising table;
a distal-end hard portion arranged at a distal end of an insertion portion configured to be inserted into a subject, the distal-end hard portion including a main body formed of resin and a housing formed of metal, wherein a groove portion accommodating the forceps raising table and a space accommodating the arm are formed, wherein the through hole is open at the other end into the space, and wherein another through hole that communicates the groove portion and the space is formed in the housing;
a cap sealing the space of the distal-end hard portion; and
a single unitary seal arranged on an outer periphery of a pillar portion of the arm, the seal including: a first portion provided to a first gap; and a second portion provided to a second gap, the seal sealing the first gap and the second gap in a watertight manner, the first gap being formed between an outer peripheral surface of the pillar portion of the arm and an inner peripheral surface defining the through hole of the housing, and the second gap being formed between the outer peripheral surface of the pillar portion of the arm and an inner peripheral surface defining the fitting groove of the forceps raising table.

\* \* \* \* \*